United States Patent [19]

Saitoh et al.

[11] Patent Number: 5,162,330
[45] Date of Patent: Nov. 10, 1992

[54] DYNEMICIN C ANTIBIOTIC, ITS TRIACETYL DERIVATIVE AND PHARMACEUTICAL COMPOSITION CONTAINING SAME

[75] Inventors: Kyoichiro Saitoh, Kanagawa; Takeo Miyaki, Yokohama; Haruaki Yamamoto; Nahomi Oda, both of Tokyo, all of Japan

[73] Assignee: Bristol-Myers Squibb Co., New York, N.Y.

[21] Appl. No.: 610,893

[22] Filed: Nov. 5, 1990

[51] Int. Cl.$^5$ ................ A61K 31/445; C07D 491/044; C07D 491/08

[52] U.S. Cl. ..................................... 514/279; 546/34; 435/119

[58] Field of Search ........................... 546/34; 514/279

[56]                  References Cited
             U.S. PATENT DOCUMENTS
    4,916,065  4/1990  Ohkuma et al. ..................... 435/119

*Primary Examiner*—Alan L. Rotman
*Attorney, Agent, or Firm*—David M. Morse

[57]                      ABSTRACT

The novel antitumor antibiotic designated herein as dynemicin C is produced by fermentation of *Micromonospora chersina* M956-1 mutant F1085 (ATCC-55077). Dynemicin C and its triacetate derivative possess antibacterial and antifungal activity and also inhibit the growth of mammalian tumors.

2 Claims, 3 Drawing Sheets

DYNEMICIN C ANTIBIOTIC, ITS TRIACETYL DERIVATIVE AND PHARMACEUTICAL COMPOSITION CONTAINING SAME

BACKGROUND OF THE INVENTION

1. Field of the Invention

This invention relates to a novel antibiotic compound designated dynemicin C and its triacetate derivative. Both compounds possess antibacterial, antifungal and antitumor activities.

2. Description of the Prior Art

Elucidation of the structure of dynemicin C revealed that it contained a conjugated di-yne moiety. This unusual functionality has been discovered in the esperamicins (*J. Am. Chem. Soc.* 109, 3462-3464, 1987) and calichemicins (*J. Am. Chem. Soc.* 109, 3464-3466, 1987 and ibid 109, 3466-3468, 1987), extraordinarily potent antitumor antibiotics produced by an Actinomadura strain (see U.S. Pat. No. 4,675,187) and a Micromonospora strain (Program and Abstracts of 26th Interscience Conference on Antimicrobial Agents and Chemotherapy, September, 1986, Abstract 227), respectively.

Esperamicins $A_1$ and $A_2$ are believed to be identical, respectively, to CL-1577A and B disclosed in U.S. Pat. No. 4,530,835. The esperamicins are also structurally related to the antibiotics WS-6049A and B disclosed in U.S. Pat. No. 4,578,271. A fragment of CL-1577A or B designated CL-1577-$B_4$ is disclosed in U.S. Pat. No. 4,661,353 while fragments of esperamicins $A_1$ or $A_2$ designated BBM-1675C and D are disclosed in U.K. Published Application 2,179,649A.

An esperamicin component designated BMY-41339 and having the formula

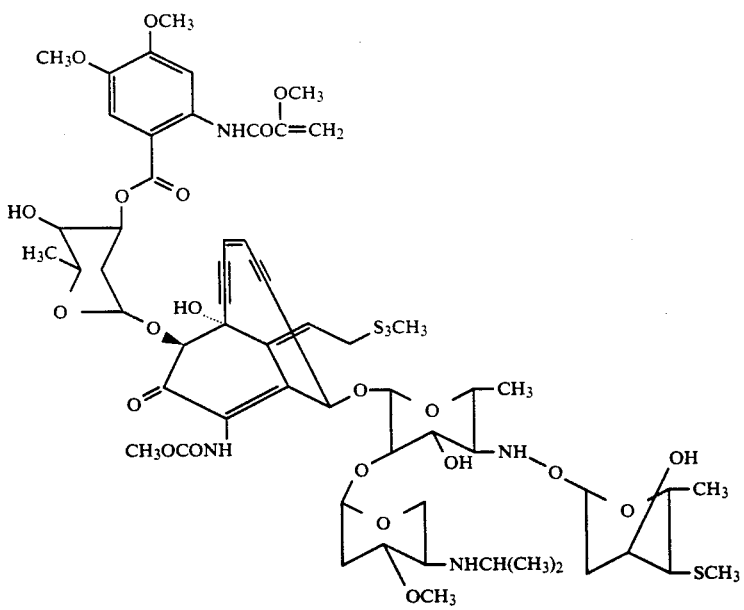

is disclosed in U.S. patent application Ser. No. 323,648 filed Mar. 15, 1989.

The antitumor antibiotics designated BU-3420T and triacetyl BU-3420T having the conjugated di-yne moiety are disclosed in U.S. Pat. No. 4,916,065. These antibiotics, also named dynemicin A and triacetyl dynemicin A, are also disclosed in *J. Antibiotics* 42 (9):1449-1452, 1989. BU-3420T (dynemicin A) is obtained from the fermentation broth of *Micromonospora chersina* strain M956-1 (ATCC-53710).

SUMMARY OF THE INVENTION

The present invention provides the antibiotic dynemicin C and its tri-O-acetyl derivative which exhibit activity against a wide range of fungi and gram-positive and gram-negative bacteria. Additionally, the compounds exhibit in vitro and in vivo antitumor activity.

Dynemicin C is obtained by cultivating a mutant strain of *Micromonospora chersina* strain M956-1. The mutant strain designated mutant F1085 was obtained by treating a spore suspension of *Micromonospora chersina* strain M956-1 with N-methyl-N'-nitro-N-nitrosoguanidine. The mutant strain F1085 is cultivated in an aqueous nutrient medium containing assimilable sources of carbon and nitrogen under submerged aerobic conditions until a substantial amount of dynemicin C is produced by said organism in said culture medium. Dynemicin C is then recovered from said culture medium by conventional procedures. The triacetate derivative of dynemicin C may be prepared by acetylation of dynemicin C such as with acetic anhydride.

In another aspect there are provided pharmaceutical compositions useful for treating bacterial or fungal infections in an animal host or for inhibiting tumors in a mammalian host comprising an effective bacterial-inhibiting, fungal-inhibiting or tumor-inhibiting amount of dynemicin C or its triacetate derivative together with a pharmaceutically acceptable carrier or diluent.

In a further aspect the present invention provides a method of treating bacterial or fungal infections in an animal host by administering to said host an effective antifungal or antibacterial amount of dynemicin C or its triacetate derivative, or a pharmaceutical composition thereof.

Finally, the present invention provides a method of inhibiting the growth of tumors in a mammalian host by administering to said host a tumor-inhibiting amount of dynemicin C or its triacetate derivative, or a pharmaceutical composition thereof.

Figure 1:
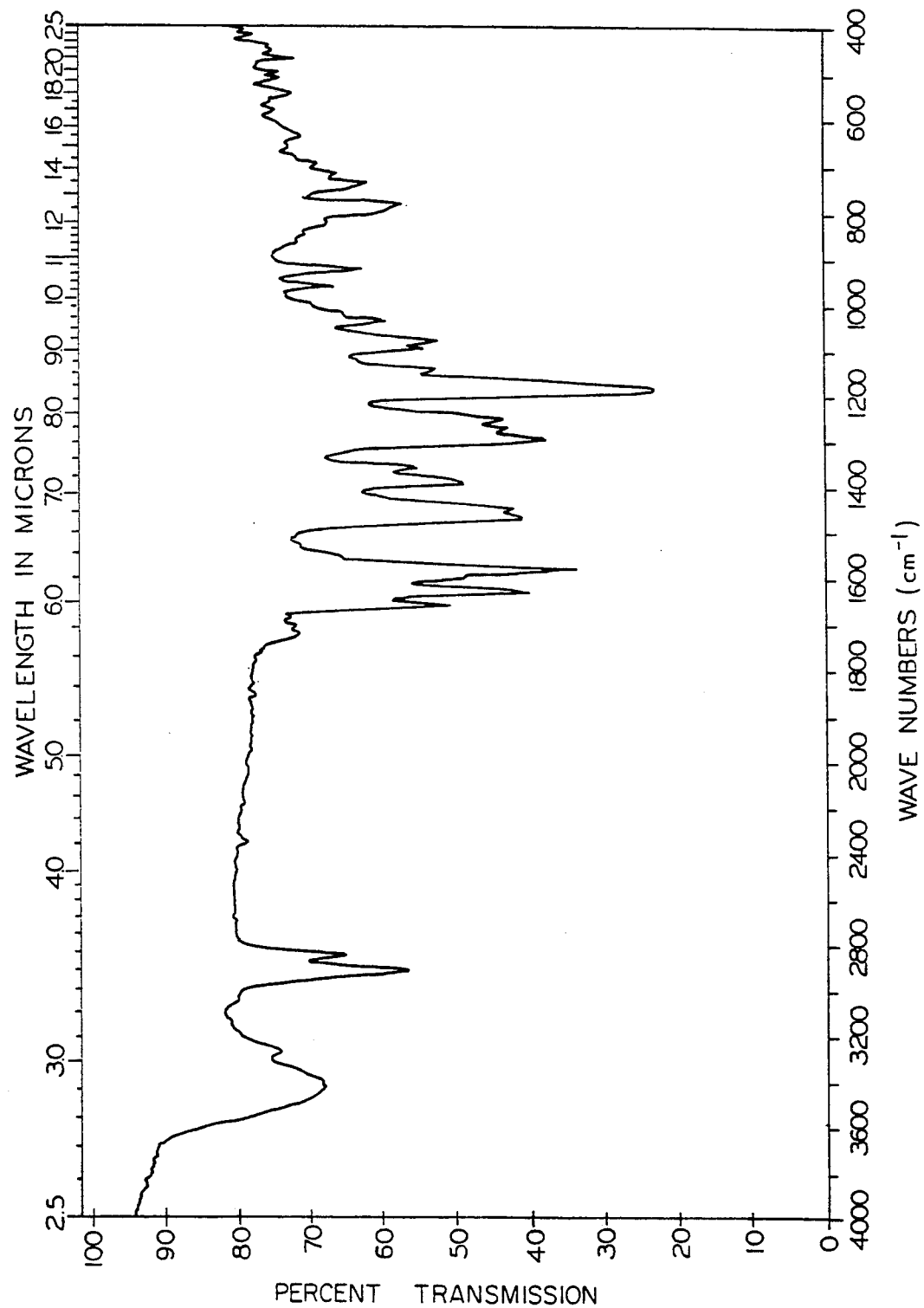
FIG. 1 represents the infrared absorption spectrum of dynemicin C (in KBr).

Sodium chloride tolerance is observed at 2% but not at 3%. The profile of sugar utilization is shown in Table 2.

The growth and sporulation of mutant strain F1085 are somewhat slower than the parent strain on the descriptive media. However, based on the above-mentioned taxonomic characterization of the mutant, distinct differences are not observed between the mutant strain, F1085, and the parent strain, M956-1.

TABLE 1

| | Cultural characteristics of a mutant strain F1085 | | | |
|---|---|---|---|---|
| Medium | Growth | Substrate mycelium | Sporulation | Diffusible pigment |
| Sucrose-nitrate agar (Czapek-Dox agar) | Moderate | Light orange (52) | Moderate; brownish black (65) | None |
| Yeast extract-malt extract agar (ISP No. 2) | Good | Colorless | Abundant; black (267) | Deep yellowish brown (75) |
| Oatmeal agar (ISP No. 3) | Moderate | Colorless | Moderate; dark yellowish brown (78) | None |
| Inorganic salts-starch agar (ISP No. 4) | Good | Dark orange yellow (72) | Poor; black (267) | None |
| Glycerol-asparagine agar (ISP No. 5) | Poor | Colorless | Poor; black (267) | None |
| Peptone-yeast extract-iron agar (ISP No. 6) | Poor | Moderate yellowish Brown (77) | Scant; dark yellowish brown (78) | None |
| Tyrosine agar (ISP No. 7) | Moderate | Colorless | Moderate; brownish black (65) | None |

Observation after incubation at 28° for 3 weeks
Color name. used: ISCC-NBS Color Name Chart

TABLE 2

| Sugar utilization of mutant F1085 and *Micromonospora chersina* strain M956-1 (ATCC-53710) | | | | | | | | |
|---|---|---|---|---|---|---|---|---|
| | F1085 | | M956-1 | | | F1085 | | M956-1 | |
| | PG | Ld | PG | Ld | | PG | Ld | PG | Ld |
| Glycerol | tr | tr | tr | — | Cellobiose | + | + | + | + |
| D-Arabinose | — | — | — | — | Melibiose | + | + | + | + |
| L-Arabinose | + | + | + | + | Trehalose | + | + | + | + |
| D-Xylose | + | + | + | + | Raffinose | + | — | + | — |
| D-Ribose | — | — | tr | — | D-Melezitose | — | — | — | — |
| L-Rhamnose | — | — | — | — | Soluble starch | + | + | + | + |
| D-Glucose | + | + | + | + | Cellulose | +(w) | — | + | — |
| D-Galactose | + | + | + | + | Dulcitol | — | — | — | — |
| D-Fructose | + | + | + | + | Inositol | — | — | tr | — |
| D-Mannose | + | + | + | + | D-Mannitol | — | tr | — | — |
| L-Sorbose | — | — | — | — | D-Sorbitol | — | — | — | — |
| Sucrose | + | + | + | + | Salicin | +(w) | + | + | tr |
| Lactose | + | + | + | +(w) | | | | | |

PG: Pridham-Gottlieb's inorganic medium (ISP No. 9) supplemented with 0.01% yeast extract.
Ld: Luedeman's yeast extract-CaCO$_3$ medium
Observation after incubation at 28° C. for 3 weeks.
Growth: tr; trace. +(w); weekly positive

DETAILED DESCRIPTION

The dynemicin C antibiotic of the present invention is produced by fermentation of *Micromonospora chersina* mutant strain F1085 or a dynemicin C-producing mutant thereof.

Strain F1085 was obtained by treating the spore suspension of *Micromonospora chersina* strain M956-1 (ATCC-53710) with N-methyl-N'-nitro-N-nitrosoguanidine.

Taxonomic Studies of Producing Organism

The mutant strain, F1085, forms single spores on the non-fragmentary vegetative mycelia grown on descriptive agar media. The surface of spores has short blunt spines. Aerial mycelium, motile spore and special vessels are not formed.

As shown in Table 1 below, the color of vegetative mycelium is colorless to orange, and turns to brown to black after sporulation. The growth temperature ranges from 18° C. to 49° C. Nitrate is not reduced to nitrite.

A biologically pure culture of mutant strain F1085 has been deposited with the American Type Culture Collection (ATCC), Washington, D.C. and added to its permanent collection of microorganisms as ATCC-55077.

Cultivation of *Micromonospora chersina* M956-1 mutant F1085 did not produce dynemicin A.

It is to be understood that the present invention is not limited to use of the particular mutant strain described above. It is especially intended to include other dynemicin C - producing mutant strains of the said organism which can be produced by conventional means such as x-radiation, ultraviolet radiation, treatment with nitrogen mustards, phage exposure, and the like.

Preparation of Dynemicin C

Dynemicin C is produced by cultivating *Micromonospora chersina* M956-1 mutant F1085 or a dynemicin C - producing mutant thereof under submerged aerobic conditions in an aqueous nutrient medium. The producing organism is grown in a nutrient medium containing an assimilable carbon source, for example L-arabinose, D-xylose, sucrose, melibiose, raffinose or soluble starch. The nutrient medium should also contain an assimilable nitrogen source such as fish meal, peptone, soybean flour, peanut meal, cottonseed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate, or like ions.

Production of dynemicin C can be effected at any temperature conducive to satisfactory growth of the producing organism, e.g. 18° C. to 49° C., and is conveniently carried out at a temperature of about 28° C.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of dynemicin C. The medium in which the vegetative inoculum is produced can be the same as, or different from, that utilized in the tank so long as it is such that a good growth of the producing organism is obtained.

In general, optimum production of dynemicin C is achieved after incubation periods of about 3–4 days. Antibiotic production may be monitored by the paper disk-agar diffusion assay using *Bacillus subtilis* as the test organism.

Isolation and Purification

Dynemicin C may be isolated from the fermentation broth by conventional isolation and purification procedures, e.g. solvent extraction and chromatography. Example 2 below illustrates a preferred isolation and purification procedure for obtaining dynemicin C in substantially pure form.

Example 3 illustrates preparation of the triacetyl derivative of dynemicin C. This derivative may be obtained by reacting dynemicin C with an acetylating agent such as acetic anhydride in an inert organic solvent.

Physicochemical Properties of Dynemicin C and Dynemicin C Triacetate

Dynemicin C was obtained as an amorphous, vivid deep purple powder. It is soluble in dimethylsulfoxide, 1,4-dioxane, dimethylformamide and acetonitrile, slightly soluble in methanol and ethyl acetate, and practically insoluble in water and n-hexane. The physicochemical properties of dynemicin C are summarized in Table 3. Dynemicin C is distinguished from dynemicin A by HPLC and TLC analyses. The UV spectrum of this component exhibited maxima at around 239, 290, 568 and 598 nm owing to the same chromophore, 1,4,6-tri-hydroxy-8,9-disubstituted anthraquinone, as dynemicin A.

Figure 3:
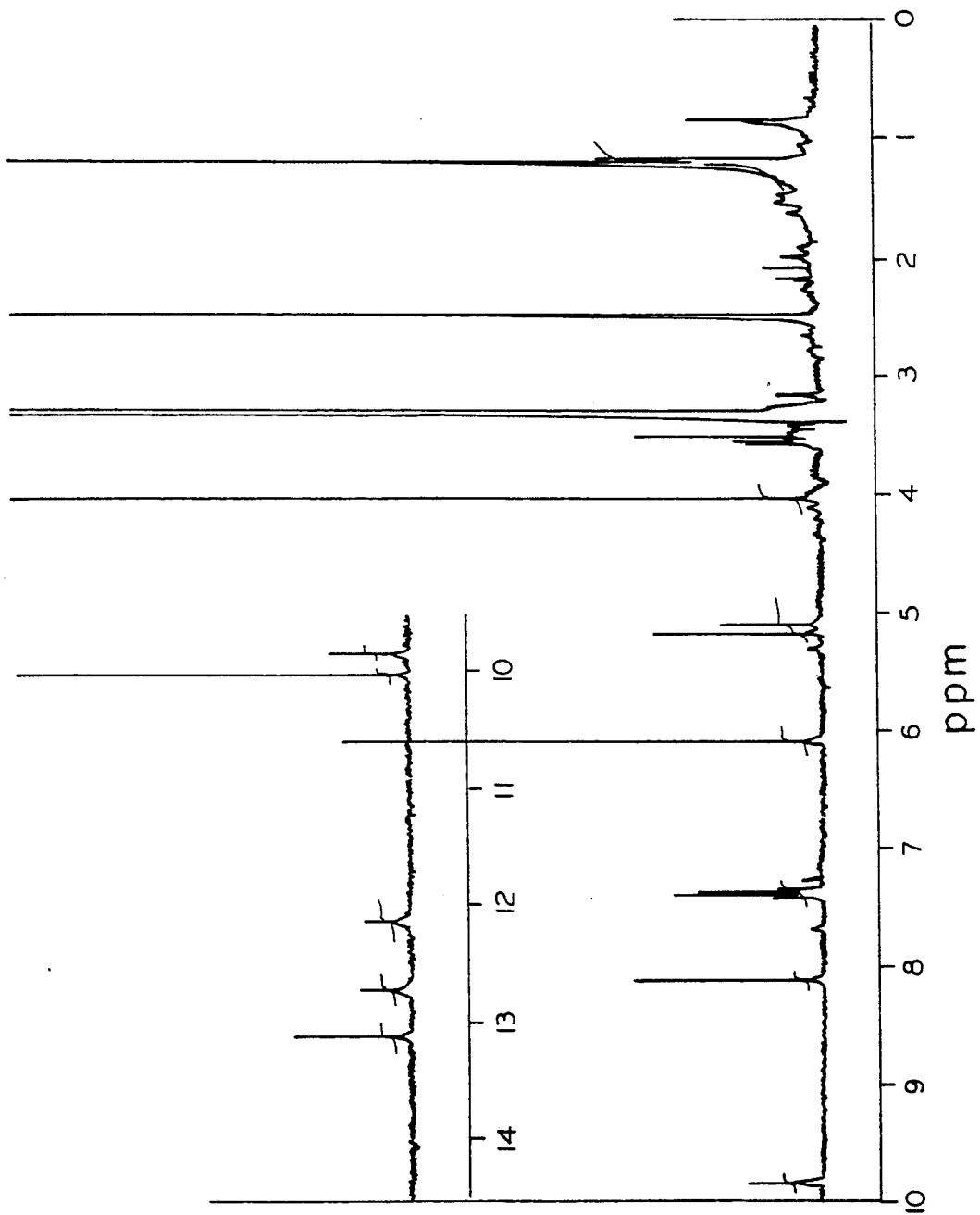
FIG. 3 represents the proton magnetic resonance spectrum of dynemicin C in DMSO-$d_6$ (400 MHz).

The molecular formula of dynemicin C was established as $C_{30}H_{19}NO_8$ based on FAB-MS (negative) [m/z 521(M)$^-$] and $^1$H-NMR spectrum (FIG. 3). The mass spectrum of dynemicin C differs from that of dynemicin A [FAB-MS(negative), m/z 537 (M)$^-$] by 16 mass units. As tabulated in Table 4, the signal (carboxylic proton) at δ: 12.30 ppm for dynemicin C vanished, while a new signal assignable to an aldehyde proton at δ: 10.03 ppm was observed in dynemicin C. The spectrum, also, showed two cis-double bond protons (δ:6.11,2H) of the 1,5-diyn-3-ene system observed in the $^1$H-NMR spectrum of dynemicin A.

Figure 2:
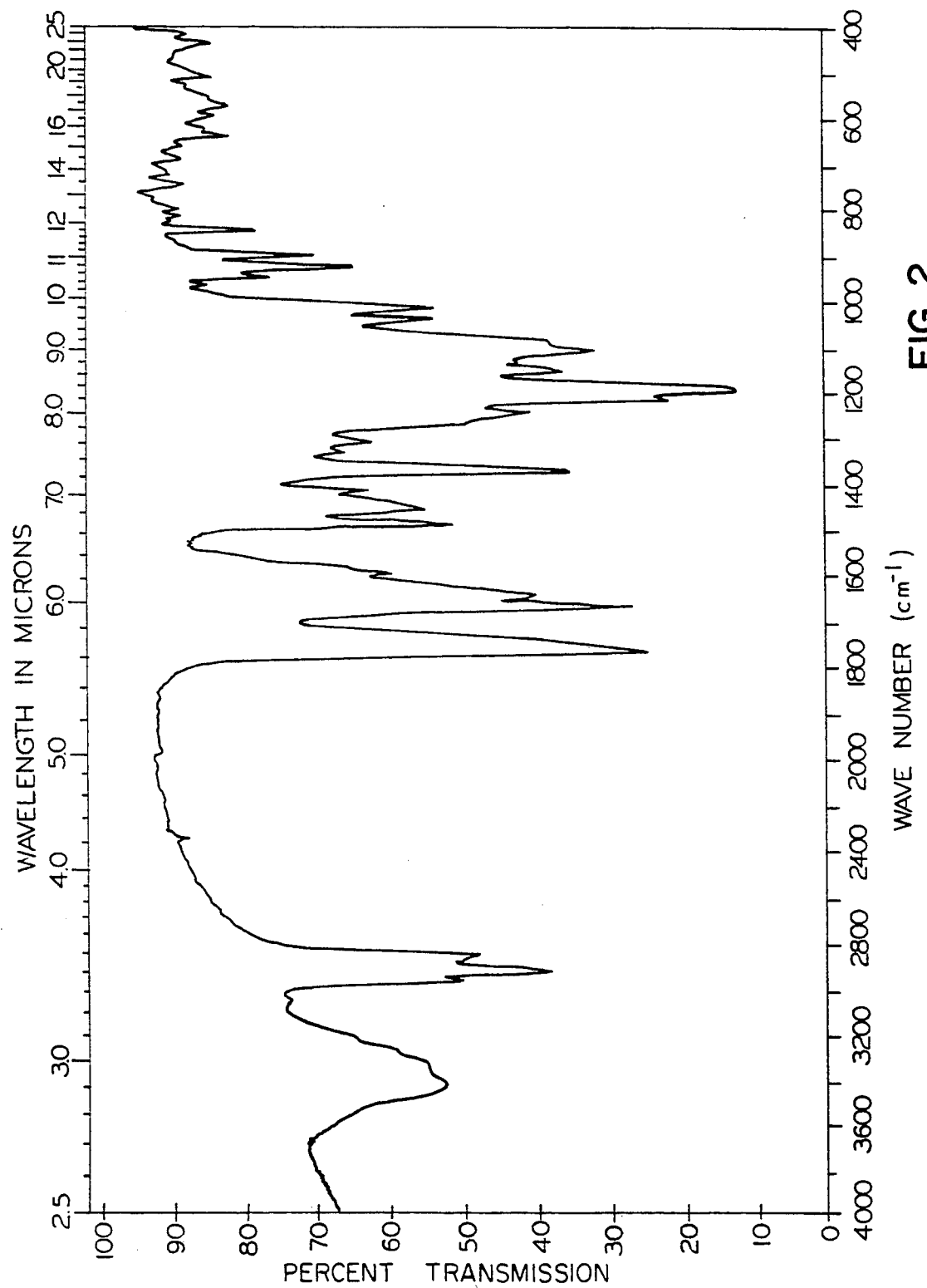
FIG. 2 represents the infrared absorption spectrum of triacetyl dynemicin C (in KBr).

The physico-chemical properties of triacetyl dynemicin C are summarized in Table 5. The IR spectrum of the acetyl derivative (FIG. 2) exhibits a strong carbonyl band at 1765 cm$^{-1}$ in addition to the bands observed on the spectrum of dynemicin C. One methyl (δ:1.18), three acetyl methyls (2.35, 2.36 and 2.44), one methoxy (4.01), three methines (3.53, 5.05, and 5.08), two olefinic (6.09×2), three aromatic protons (7.62×2 and 8.08) and one aldehyde proton (10.02) were observed in the $^1$H-NMR spectrum (Table 6). Corresponding carbon signals were also found in the $^{13}$C-NMR spectrum. Among the quaternary carbons, four carbons appeared at δ89.6, 89.7, 97.5 and 97.6 strongly suggesting a conjugated diyne system from spectral comparison with esperamicin. Each carbon signal also showed relatively good correlation with the corresponding carbon of triacetyl dynemicin A except the aldehyde carbon signal. Carboxylic carbon of triacetyl dynemicin A was resonated at δ167.3(s), while an aldehyde carbonyl signal of triacetyl dynemicin C was observed at δ188.0(d) in the $^{13}$C-NMR spectrum (Table 7). Consequently, the structures of dynemicin C and triacetyl dynemicin C were concluded to have an aldehyde group in place of the carboxyl group at C-5 of dynemicin A, i.e.

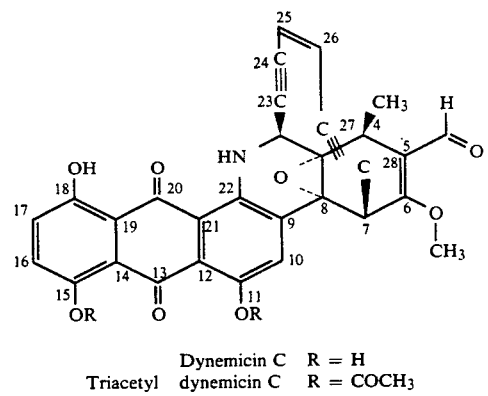

Dynemicin C R = H
Triacetyl dynemicin C R = COCH$_3$

TABLE 3

| Physico-chemical properties of dynemicin C | |
| --- | --- |
| Nature | Vivid deep purple amorphouse powder |
| M.P. | >230° C. (dec) |
| FAB-MS (negative) m/z | 521 (M)$^-$ |
| Molecular formula | $C_{30}H_{19}NO_8$ |
| UV λmax nm (ε) in MeOH | 286sh(6,800), 570(8,200), 600 (7,800) |
| IR (KBr) cm$^{-1}$ | 3430, 2930, 1730, 1665, 1630, 1580, 1475, 1460, 1400, 1300, 1190 |
| TLC, SiO$_2$ Rf | 0.86 |
| (N-103, xylene-methyl ethyl ketone-methanol = 5:5:1, v/v) | |
| | cf. dynemicin A: 0.30, L: 0.15, M: 0.63, N: 0.08 |
| HPLC Rt (min.) | 9.62 |
| (ODS, CH$_3$CN—MeOH-0.15% KH$_2$PO$_4$, PH 3.50 = 3:3:2, v/v) | |
| | cf. dynemicin A: 6.13, L: 4.72, M: 4.42, N: 3.80 |

FAB-MS: Fast atom bombardment mass spectrum

TABLE 4

$^1$H-NMR spectrum of dynemicin C and A (400 MHz)

| Dynemicin C (δppm in DMSO-$d_6$) | Dynemicin A (δppm in DMsO-$d_6$) |
|---|---|
| *13.12 (1H, s) | *13.10 (1H, br) |
| *12.72 (1H, s) | *12.70 (1H, br) |
|  | *12.30 (1H, br) |
| *12.41 (1H, s) | *12.15 (1H, br) |
| 10.03 (1H, s) |  |
| *9.86 (1H, d, J=4.3) | *9.86 (1H, d, J=4.3) |
| 8.12 (1H, s) | 8.03 (1H, s) |
| 7.42 (1H, d, J=9.4) | 7.38 (1H, d, J=8.9) |
| 7.36 (1H, d, J=9.4) | 7.33 (1H, d, J=8.9) |
| 6.11 (2H, s like) | 6.09 (1H dd, J=9.8, 1.3) |
|  | 6.06 (1H, dd, J=9.8, 1.3) |
| 5.18 (1H, s) | 4.89 (1H, s) |
| 5.10 (1H, d, J=4.3) | 5.08 (1H, d, J=4.3) |
| 4.03 (3H, s) | 3.82 (3H, s) |
| 3.55 (1H, q, J=7.3) | 3.57 (1H, q, J-7.3) |
| 1.21 (3H, d, J=7.3) | 1.30 (3H, d, J=7.3) |

*disappeared on $D_2O$ addition

TABLE 5

Physico-chemical properties of triacetyldynemicin C

| | |
|---|---|
| Nature | Orange amorphous powder |
| M.P. | 230° C. (dec) |
| FAB-MS (negative) m/z | 647 (M)$^-$ |
| Molecular formula | $C_{36}H_{25}NO_{11}$ |
| UV λmax nm (ε) in MeOH | 247(20,700), 480(3,800) |
| IR (KBr) cm$^{-1}$ | 2930, 1765, 1665, 1640, 1600, 1490, 1460, 1375, 1190 |
| HPLC Rt (min.) | 2.77 |
| (ODS, $CH_3CN$—MeOH-0.15% $KH_2PO_4$, PH 3.50 = 3:3:2, v/v) | cf. dynemicin A: 6.11 triacetyldynemicin A: 2.84, dynemicin C: 9.36 |

TABLE 6

$^1$H-NMR spectrum of triacetyldynemicin C (400 MHz in DMSO-$d_6$)

| Proton No. | Triacetyldynemicin C |
|---|---|
| 4-$CH_3$ | 1.18(3H, d, J=7.3Hz) |
| 11-$OCOCH_3$, 15-$OCOCH_3$, | 2.35(3H, s), 2.36(3H, s), |
| 18-$OCOCH_3$ | 2.44(3H, s) |
| 4-H | 3.53(1H, m) |
| 6-$OCH_3$ | 4.01(3H, s) |
| 7-H | 5.08(1H, s) |
| 2-H | 5.05(1H, d, J=4.3Hz) |
| 25 & 26-H | 6.09(2H, s) |
| 16 & 17-H | 7.62(2H, s) |
| 10-H | 8.08(1H, s) |
| 1-NH | 9.42(1H, d, J=4.3Hz) |
| 5-CHO | 10.02(1H, s) |

TABLE 7

$^{13}$C-NMR spectrum of triacetyldynemicin C and triacetyldynemicin A

| Triacetyldynemicin C (δppm in DMSO-$d_6$) | Triacetyldynemicin A (δppm in DMSO-$d_6$) |
|---|---|
| 17.2 (q) | 18.5 (q) |
| 20.7 (q × 2) | 20.6 (q × 2) |
| 21.0 (q) | 20.9 (q) |
| 30.2 (d) | 31.4 (d) |
| 31.6 (d) | 35.6 (d) |
| 43.9 (d) | 43.8 (d) |
| 57.7 (q) | 57.7 (q) |
| 62.8 (s) | 63.0 (s) |
| 71.5 (s) | 71.3 (s) |
| 89.6 (s) | 88.8 (s) |
| 89.7 (s) | 89.6 (s) |
| 97.5 (s) | 97.3 (s) |
| 97.6 (s) | 99.4 (s) |
| 115.0 (s × 2) | 114.7 (s) |
|  | 114.8 (s) |
| 123.8 (d) | 124.0 (d) |
| 124.7 (s) | 124.5 (s) |
| 125.1 (d) | 124.4 (d) |
| 126.0 (s) | 125.9 (s) |
| 126.1 (s) | 126.1 (s) |
| 130.1 (d) | 130.0 (d) |
| 129.9 (s) | 130.1 (s) |
| 130.7 (d) | 130.6 (d) |
| 131.1 (d) | 131.0 (d) |
| 139.5 (s) | 139.5 (s) |
| 143.9 (s) | 143.8 (s) |
| 146.5 (s) | 146.4 (s) |
| 147.0 (s) | 146.9 (s) |
| 159.4 (s) | 153.2 (s) |
|  | 167.3 (s) |
| 169.0 (s) | 168.9 (s) |
| 169.3 (s × 2) | 169.1 (s × 2) |
| 180.7 (s) | 180.6 (s) |
| 182.8 (s) | 182.7 (s) |
| 188.0 (d) |  |

Biological Activity of Dynemicin C and its Triacetate Derivative

In Vitro Antibacterial and Antifungal Activities

The minimum inhibitory concentration (MIC) was determined by a two-fold serial tube dilution method using nutrient agar (pH7, Difco containing $10^5$ cfu/ml). After incubation at 32° C. for 18 hours, the MIC was determined.

Dynemicin C and its triacetate showed strong activity against gram-positive organisms. Both compounds had much better activities against these organisms than amikacin. Against gram-negative organisms including seven strains of Pseudomonas and two strains of Xanthomonas, dynemicin C triacetate showed activity in the range of MIC 0.05–0.8 mcg/ml. Although dynemicin C did not show any activity against *Pseudomonas aeruginosa* species, for other gram-negatives except *Enterobacter cloacae* IPM-12 and *Serratia marcescens* IPM-16, dynemicin C revealed activity better than amikacin.

TABLE 8

Antibacterial spectrum of dynemicins

| | MIC (mcg/ml) | | | |
|---|---|---|---|---|
| Test organism | Dynemicin A | Dynemicin C | Dynemicin C triacetate | Amikacin |
| S. aureus smith | <0.000025 | <0.0002 | 0.0008 | 1.6 |
| S. aureus A15036 (MRSA) | <0.000025 | <0.0002 | 0.0004 | 3.1 |
| S. aureus IPM-24 (MRSA) | <0.000025 | <0.0002 | 0.0004 | 100 |
| S. epidermidis 11-1230 | <0.000025 | <0.0002 | 0.0008 | 25 |
| E. faecalis A9808 | <0.000025 | 0.0008 | 0.0063 | 50 |
| E. faecium A24817 | <0.000025 | 0.0008 | 0.0063 | 100 |
| M. luteus PCI 1001 | <0.000025 | 0.0008 | 0.0031 | 3.1 |

TABLE 8-continued

Antibacterial spectrum of dynemicins

| Test organism | MIC (mcg/ml) | | | |
|---|---|---|---|---|
| | Dynemicin A | Dynemicin C | Dynemicin C triacetate | Amikacin |
| E. coli Juhl A15119 | 0.0032 | 100 | 0.4 | 12.5 |
| E. coli 255 | 0.0032 | 100 | 0.4 | 6.3 |
| K. pneumoniae PCI 602 | 0.0032 | 0.8 | 0.2 | 1.6 |
| P. mirabilis IFO 3849 | 0.0016 | 0.8 | 0.2 | 25 |
| P. vulgaris IPM-13 | 0.0008 | 0.05 | 0.1 | 6.3 |
| M. morganii I510 | 0.0008 | 0.1 | 0.05 | 25 |
| P. rettgeri IPM-14 | 0.0008 | 0.1 | 0.1 | 12.5 |
| E. cloacae IPM-12 | 0.0016 | 100 | 0.8 | 25 |
| S. marcescens IPM-15 | 0.0032 | 25 | 0.8 | 12.5 |
| S. marcescens IPM-16 | 0.0032 | 100 | 0.4 | 100 |
| P. aeruginosa A9843A | 0.0016 | 100 | 0.2 | 3.1 |
| P. aeruginosa A20599 | 0.0032 | 100 | 0.4 | 1.6 |
| P. aeruginosa KKA19 | 0.0032 | 100 | 0.4 | 3.1 |
| P. aeruginosa IPM-8 | 0.0032 | 100 | 0.4 | 6.3 |
| P. aeruginosa IPM-9 | 0.0063 | 100 | 6.3 | 1.6 |
| X. maltophilia GN12873 | 0.0016 | 100 | 0.8 | >100 |
| X. maltophilia No. 661 | 0.0008 | 1.6 | 0.2 | >100 |
| P. cepecia No. 651 | 0.0008 | 0.1 | 0.2 | >100 |
| P. cepecia A21213 | 0.0008 | 0.1 | 0.2 | >100 |

The antifungal MICs of dynemicin C and its triacetate were determined by an agar dilution method on yeast morphology agar adjusted to pH7.0 with 1/15M phosphate buffer. A 5 μl aliquot of fungal suspension containing $10^6$ cells/ml was inoculated onto the surface of the antibiotic-containing agar plates with a multiinoculator. After incubation at 28° C. for 40 hours, the lowest concentration of antibiotic causing virtually complete inhibition of fungal growth (MIC) was determined.

Dynemicin C and dynemicin C triacetate showed activity against an amphotericin resistant strain of Candida albicans ATCC 38247 of MIC 0.8 mcg/ml and 0.4 mcg/ml, respectively, and those activities were stronger than that of ketoconazole. Against Cryptococcus neoformans D49 and C. neoformans IAM4514, dynemicin C was much more active than amphotericin B and ketoconazole but dynemicin C triacetate was inactive for these two strains.

TABLE 9

Antifungal spectrum of dynemicins

| Test Organism | MIC(mcg/ml) | | | | |
|---|---|---|---|---|---|
| | Dynemicin A | Dynemicin C | Dynemicin C triacetate | Amphotericin B | Keto-conazole |
| Canadia albicans* ATCC 38247 | <0.0031 | 0.8 | 0.4 | 50 | 6.3 |
| Cryptococcus neoformans D49 | 0.2 | 0.0063 | >100 | 0.2 | 0.1 |
| Cryptococcus neoformans IAM 4514 | 0.2 | 0.013 | <100 | 0.4 | 0.1 |

*Amphotericin resistant strain

Antitumor Activity

Dynemicin C and its triacetate derivative were tested for in vitro cytotoxicity against murine and human tumor cell lines. Dynemicin A and its triacetate derivative were used as reference compounds. B16-F10 (murine melanoma) cells were grown to the logarithmic phase in enriched Eagle minimum essential medium (MEM) supplemented with fetal calf serum (FCS, 10%) and kanamycin (60 mcg/ml) and HCT-116 (human colon carcinoma) cells in Maccoy's 5A medium supplemented with FCS (10%), penicillin (100 μ/ml) and streptomycin (100 mcg/ml), and were harvested and inoculated into wells of the 96- or 24-well tissue culture plate with test materials at concentrations of $1.5 \times 10^4$, $1.3 \times 10^4$, $1.3 \times 10^4$, $2.5 \times 10^4$ and $3.0 \times 10^4$ cells/ml., respectively. They were incubated at 37° C. in a humidified atmosphere of 5% $CO_2$ and 95% air for 72 hours. The cytotoxic activities were determined colorimetrically at 540 nm after staining viable cells with 0.006% neutral red solution. The results are summarized in Table 10 in terms of $IC_{50}$.

Dynemicin C demonstrated almost the same activity as dynemicin A, while the acetates of these compounds showed potent activity against B16 melanoma.

TABLE 10

Cytotoxic Activity of Dynemicins

| Compound | $IC_{50}$ (μg/ml) | |
|---|---|---|
| | B16-F10 | HCT-116 |
| Dynemicin C | 0.0028 | 0.0086 |
| Dynemicin A | 0.0052 | 0.0032 |
| Dynemicin C acetate | 0.00074 | 0.0028 |
| Dynemicin A acetate | 0.0007 | Not Tested |

B16-F10: mouse melanoma B16-F10
HCT-116: human colon carcinoma HCT-116

As shown above dynemicin C and its triacetyl derivative possess potent antibacterial and antifungal activity and are thus useful in the therapeutic treatment of mammals and other animals for diseases caused by such organisms. Additionally the compounds may be utilized for other conventional applications of antimicrobial agents such as disinfecting medical and dental equipment.

Dynemicin C and its triacetyl derivative are also therapeutically useful in inhibiting the growth of malignant tumors in mammalian hosts.

The present invention, therefore, provides a method for therapeutically treating an animal host affected by a bacterial or fungal infection which comprises administering to said host an effective antibacterial or antifungal dose of dynemicin C or dynemicin C triacetate, or a pharmaceutical composition thereof.

Also provided is a method for inhibiting the growth of malignant tumors in mammals which comprises administering to said mammalian host an effective tumor-inhibiting dose of dynemicin C or dynemicin C triacetate, or a pharmaceutical composition thereof.

In another aspect the present invention provides a pharmaceutical composition which comprises an effective antibacterial or antifungal amount of dynemicin C or dynemicin C triacetate in combination with a pharmaceutically acceptable carrier or diluent.

Additionally, the invention provides a pharmaceutical composition which comprises an effective tumor-inhibiting amount of dynemicin C or dynemicin C triacetate in combination with a pharmaceutically acceptable carrier or diluent.

The pharmaceutical compositions may contain other active antimicrobial or antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other suitable sterile injectable medium immediately before use.

For use as an antimicrobial agent, the dynemicin C or dynemicin C triacetate, or pharmaceutical composition thereof, is administered so that the concentration of active ingredient is greater than the minimum inhibitory concentration for the particular organism being treated. For use as an antitumor agent, optimal dosages and regimens of dynemicin C and dynemicin C triacetate for a given mammalian host can be readily ascertained by those skilled in the art. It will, of course, be appreciated that the actual dose of compound used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are provided for illustrative purposes only and are not intended to limit the scope of the invention. Unless otherwise indicated, all volume ratios used are volume/volume.

EXAMPLE 1

Fermentation of Dynemicin C

A well grown slant culture of strain F1085 was used to inoculate five 500-ml Erlenmeyer flasks each containing 150 ml of seed medium composed of lactose 1%, soluble starch 3%, fish meal 1%, $CaSO_4$ 0.6% and $CaCO_3$ 0.5% (pH 7.0). The seed flasks were incubated at 32° C. for four days on a rotary shaker (200 rpm) and 500 ml of the seed culture was transferred to a 20-liter stir-jar fermentor containing 12 liters of production medium consisting of corn starch 1%, Pharmamedia 0.5%, $CaCO_3$ 0.1%, $CuSO_4.5H_2O$ 0.005% and NaI 0.00005%, the pH being adjusted to 7.0 after sterilization. The fermentor was operated at 30° C. for 90 hours under agitation of 250 rpm with an aeration rate of 12 liters per minute. The antibiotic production in the fermentation broth was monitored by the paper-disc agar diffusion assay using *Bacillus subtilis* PCI219 as the indicator organism. TLC and HPLC were also used for analysis of each component.

EXAMPLE 2

Isolation and Purification of Dynemicin C

The harvested broth (52 L) obtained according to the general procedure of Example 1 was extracted with n-butanol (28 L). The mixture was separated into mycelial cake, aqueous layer and n-butanol layer by a sharples type centrifuge. The solvent extract (25 L) was concentrated in vacuo to a small volume and then the concentrate was added to ethyl acetate (1L) to deposit a biologically inactive solid. After the impurities were removed by filtration, the filtrate was washed with water (3.2 L) and dried to afford a dark brown oily material (33.6 g). The crude material was dissolved in 360 ml of ethyl acetate-ethanol-water (6:10:20) and adsorbed on sepabeads SP-800 (Mitsubishi Kasei, 100 ml) in a batch-wise operation. After being washed with water (450 ml) and 450 ml each of aqueous methanol (50% and 80%), the activity was eluted with 80% aqueous acetone (920 ml) and concentrated in vacuo to give a dark green oily substance (3.6 g). The oily substance containing dynemicin C was chromatographed on a column of Sephadex LH-20 ($\phi 2.5 \times 40$ cm) using methanol-ethyl acetate (1:1) as the developing solvent. Upon monitoring by TLC ($SiO_2$, xylene-methyl ethyl ketone-methanol=5:5:1, v/v), the appropriate fractions were dried to yield 215 mg of dark violet hygroscopic solid. This solid was dissolved in 2 ml of 1,4-dioxane and subjected to reversed phase silica gel (ODS, A60, 350/250 mesh, Yamamura Chemical Lab., $\phi 2.5 \times 35$ cm) which had been equilibrated with 80% aqueous methanol. The column was developed with 80% aqueous methanol and 80% aqueous acetone and the eluate was monitored by HPLC [YMC gel (ODS), $A_{301}$-3, 4.6 mm I.D. $\times 100$ mm, 3 $\mu$m, Yamamura Chemical Lab.; acetonitrile-0.15% $KH_2PO_4$, pH 3.5 (75:25, v/v) as mobile phase at a flow rate of 0.8 ml/min.; UV absorption at 595 nm as detection]. The active fractions were collected and dried to give a semi-pure solid of dynemicin C (10.3 mg). The sample was subjected to Sephadex LH-20 column ($\phi 4.2 \times 30$ cm) chromatography with acetonitrile to afford dynemicin C as a homogeneous vivid deep purple powder (3 mg).

EXAMPLE 3

Triacetyl dynemicin C

Dynemicin C (12 mg) was treated with acetic anhydride (0.5 ml) in pyridine (1.0 ml) for 22 hours at room temperature. The reaction mixture was concentrated in vacuo by addition of toluene to remove the solvents. The residue was dissolved in 0.5 ml of $CH_2Cl_2$-MeOH (1:1) and the solution was applied on a silica gel plate (Merck, Kiesel gel $60F_{254}$, $20 \times 20$ cm). The plate was developed with xylene-methyl ethyl ketone (1:1) and the desired part (Rf 0.65-0.85) was scraped out and eluted with 60 ml of CH$_2$Cl$_2$-MeOH (5:1). The eluate was evaporated in vacuo to afford homogeneous triacetyl dynemicin C (9.5 mg) having increased solubility relative to dynemicin C.

What is claimed is:

1. The compound designated dynemicin C having the formula

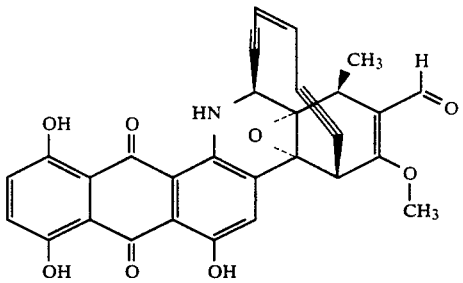

or its triacetate derivative thereof.

2. A pharmaceutical composition comprising an effective amount of dynemicin C or its triacetate derivative thereof according to claim 1 in combination with a pharmaceutically acceptable carrier or diluent.